United States Patent
Amthor et al.

(10) Patent No.: US 12,002,059 B2
(45) Date of Patent: Jun. 4, 2024

(54) ROLE-SPECIFIC PROCESS COMPLIANCE ALERT SYSTEM

(71) Applicant: KONINKLIJKE PHILIPS N.V., Eindhoven (NL)

(72) Inventors: Thomas Erik Amthor, Hamburg (DE); Joachim Dieter Schmidt, Hamburg (DE); Jörn Borgert, Hamburg (DE); Michael Günter Helle, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 60 days.

(21) Appl. No.: 17/618,563

(22) PCT Filed: Jun. 12, 2020

(86) PCT No.: PCT/EP2020/066300
§ 371 (c)(1),
(2) Date: Dec. 13, 2021

(87) PCT Pub. No.: WO2020/254203
PCT Pub. Date: Dec. 24, 2020

(65) Prior Publication Data
US 2022/0245649 A1    Aug. 4, 2022

Related U.S. Application Data

(60) Provisional application No. 62/863,437, filed on Jun. 19, 2019.

(51) Int. Cl.
*G06Q 30/018* (2023.01)
*G06Q 10/0631* (2023.01)
*G06Q 10/0633* (2023.01)

(52) U.S. Cl.
CPC ... *G06Q 30/018* (2013.01); *G06Q 10/063118* (2013.01); *G06Q 10/0633* (2013.01)

(58) Field of Classification Search
CPC .......................................... G06Q 10/00–50/00
(Continued)

(56) References Cited

U.S. PATENT DOCUMENTS 9,092,802 B1 * 7/2015 Akella ..................... G06F 16/36
10,431,336 B1 * 10/2019 Murrish ................. G16H 50/20
(Continued)

FOREIGN PATENT DOCUMENTS

| WO | WO2014100557 A2 | 6/2014 |
| WO | WO2014100557 A3 | 6/2014 |

(Continued)

OTHER PUBLICATIONS

PCT International Search Report, International application No. PCT/EP2020/066300, dated Aug. 4, 2020.
(Continued)

Primary Examiner — Alan S Miller

(57) ABSTRACT

A non-transitory computer readable medium (26) stores instructions executable by at least one electronic processor (20) to perform a medical process or workflow compliance monitoring method (100). The method includes: monitoring (102) progress of an in-progress instance of a medical process or workflow using a Business Process Model (BPM) that includes a number of defined roles in the medical process or workflow; extracting (104) a non-compliance vector (c) from the BPM during the monitoring of the in-progress instance, the non-compliance vector comprising vector elements storing values of non-compliance metrics for the in-progress instance; converting (106) the non-compliance vector to a role assignments vector (a) whose vector elements store values indicative of role assignments for remediating non-compliance of the in-progress instance;
(Continued)

and generating (108) one or more alerts directed to one or more roles on the basis of the vector elements of the role assignments vector.

20 Claims, 2 Drawing Sheets

(58) Field of Classification Search
USPC .............................................. 705/7.11–7.42
See application file for complete search history.

(56) References Cited

U.S. PATENT DOCUMENTS

| | | | | |
|---|---|---|---|---|
| 10,861,604 | B2* | 12/2020 | Bates | G16H 50/20 |
| 2002/0077792 | A1* | 6/2002 | Qiu | G06Q 30/02 |
| | | | | 703/2 |
| 2007/0132597 | A1* | 6/2007 | Rodgers | G06Q 10/10 |
| | | | | 348/E7.078 |
| 2008/0040160 | A1 | 2/2008 | Scherpbier | |
| 2009/0228309 | A1* | 9/2009 | Moll | G06Q 10/06 |
| | | | | 705/7.12 |
| 2011/0295621 | A1* | 12/2011 | Farooq | G16H 50/20 |
| | | | | 705/3 |
| 2012/0154582 | A1* | 6/2012 | Johnson | G06Q 10/00 |
| | | | | 340/521 |
| 2013/0304499 | A1 | 11/2013 | Rangadass | |
| 2014/0072193 | A1* | 3/2014 | Motomura | G06T 7/0012 |
| | | | | 382/128 |
| 2014/0244295 | A1 | 8/2014 | Carroll | |
| 2018/0181716 | A1 | 6/2018 | Mander | |

FOREIGN PATENT DOCUMENTS

| | | |
|---|---|---|
| WO | WO2015084743 A1 | 6/2015 |
| WO | WO2015164776 A1 | 10/2015 |

OTHER PUBLICATIONS

Weidlich M. et al., "Process Compliance Analysis Based on Behavioural Profiles", Queensland University of Technology (QUT), Information Systems, vol. 36, No. 7, pp. 1009-1025, Feb. 2011.

* cited by examiner

ROLE-SPECIFIC PROCESS COMPLIANCE ALERT SYSTEM

CROSS-REFERENCE TO PRIOR APPLICATIONS

This application is the U.S. National Phase application under 35 U.S.C. § 371 of International Application No. PCT/EP2020/066300, filed on Jun. 12, 2020, which claims the benefit of U.S. Application Ser. No. 62/863,437, filed on Jun. 19, 2019. These applications are hereby incorporated by reference herein.

FIELD

The following relates generally to the medical process or workflow arts, medical process or workflow monitoring arts, medical process or workflow compliance arts, medical alerting arts, and related arts.

BACKGROUND

Medical process or workflow process compliance is of increasing importance as an indicator for clinical and operational quality. Algorithms for the compliance analysis of complex processes have been published (see, e.g., Weidlich et al., Process compliance analysis based on behavioral profiles, Information Systems 36 (2011) 1009-1025).

Medical processes or workflows rely upon closely interweaved activities of numerous actors. For example, actors in a process or workflow for an in-patient radiology examination may include: the ordering physician writing out the order; clerical staff of the physician's office or medical department conveying the order to the radiology department; clerical staff at the radiology department scheduling the radiology examination; nursing staff in the patient's ward preparing the patient for the radiology examination (possibly including actions such as, for example, drawing a blood sample for testing ahead of the examination); a hematology laboratory performing one or more ancillary blood tests on the blood sample ahead of the radiology examination; hospital orderly, nursing assistant, or other hospital personnel charged with transporting the patient to the radiology laboratory for the examination; clerical staff at the radiology laboratory performing patient check-in prior to examination; a computed tomography (CT) scanner, magnetic resonance imaging (MRI) scanner, or other medical imaging device assigned for performing the radiology examination (here the "actor" is a piece of medical equipment); a radiology contrast agent to be used in the examination (here the "actor" is a consumable medical supply); a radiology technician who uses the imaging device to perform the radiology examination including administering the contrast agent at the appropriate time ahead of the imaging data acquisition and performing initial review of the acquired images to assure image quality and so forth); clerical staff at the radiology laboratory performing patient check-out after the radiology examination is complete; transport hospital personnel returning the patient to the patient's ward (likely in coordination with nursing staff at the patient's ward); a radiologist whose task list the radiology examination is assigned, who then reads the radiology examination and prepares a radiology report on same; and physician's office or medical department who receive notification that the radiology report is available.

For a smooth process or workflow, the various actors need to be in compliance with various design-basis parameters of the process or workflow. For example, the process or workflow may assume that the patient is prepared and ready for transport from the patient's ward to the radiology lab no less than forty-five minutes before the examination appointment time. If the nursing staff is delayed in preparing the patient, this will adversely impact many downstream actors including the patient transport staff, clerical staff at the radiology lab, the imaging technician, and the imaging device (which may be left unused for some time interval due to the delay, costing the hospital valuable up-time). Existing systems for monitoring medical processes or workflows sometimes fail to provide timely alerts to hospital personnel so as to mitigate the impact of noncompliance events. For example, the nursing staff may notify the orderly who arrives (on time) to transport the patient that the patient is not yet ready—but this information may not be immediately conveyed to the clerical staff of the radiology lab. Similarly, existing systems for monitoring medical processes or workflows sometimes fail to efficiently implement a remediation plan for mitigating the impact of noncompliance events. For example, if radiology examinations are scheduled in half-hour time blocks, and the delay in preparing the patient at the patient's ward will result in a fifty minute delay in delivering the patient to the radiology department, then an effective remediation plan might be to reschedule the patient for one hour later and to re-schedule the appointment at that one-hour later block into the half-hour time slot originally scheduled for the patient. But such a remediation plan can only be executed if the radiology department receives timely notification of the delay and a reasonably accurate estimate of the duration of that delay.

The following discloses new and improved systems and methods to overcome these problems and others.

SUMMARY

In one disclosed aspect, a non-transitory computer readable medium stores instructions executable by at least one electronic processor to perform a medical process or workflow compliance monitoring method. The method includes: monitoring progress of an in-progress instance of a medical process or workflow using a Business Process Model (BPM) that includes a number of defined roles in the medical process or workflow; extracting a non-compliance vector from the BPM during the monitoring of the in-progress instance, the non-compliance vector comprising vector elements storing values of non-compliance metrics for the in-progress instance; converting the non-compliance vector to a role assignments vector whose vector elements store values indicative of role assignments for remediating non-compliance of the in-progress instance; and generating one or more alerts directed to one or more roles on the basis of the vector elements of the role assignments vector.

In another disclosed aspect, a process compliance system for determining compliance with a medical process or workflow includes at least one electronic processor, and a non-transitory computer readable medium storing instructions executable by the least one electronic processor to perform a medical process or workflow compliance monitoring method. The instructions include: instructions for monitoring progress of an in-progress instance of a medical process or workflow using a BPM that includes a number of defined roles in the medical process or workflow; instructions for extracting a non-compliance vector from the BPM during the monitoring of the in-progress instance, the non-compliance vector comprising vector elements storing values of non-compliance metrics for the in-progress instance, the non-compliance vector having n elements corresponding to n non-compliance metrics; instructions for converting the non-compliance vector to a role assignments vector whose vector elements store values indicative of role assignments for remediating non-compliance of the in-progress instance, the role assignments vector having m elements corresponding to m roles, the converting including multiplying the non-compliance vector by an m×n transformation matrix; and instructions for generating one or more alerts directed to one or more roles on the basis of the vector elements of the role assignments vector based on a determination of a type of non-compliance from the non-compliance vector.

In another disclosed aspect, a medical process or workflow compliance monitoring method includes: monitoring progress of an in-progress instance of a medical process or workflow using a BPM that includes a number of defined roles in the medical process or workflow; extracting a non-compliance vector from the BPM during the monitoring of the in-progress instance, the non-compliance vector comprising vector elements storing values of non-compliance metrics for the in-progress instance; converting the non-compliance vector to a role assignments vector whose vector elements store values indicative of role assignments for remediating non-compliance of the in-progress instance; and generating one or more alerts directed to one or more roles on the basis of the vector elements of the role assignments vector, the generating including triggering a remediation prediction model for corresponding one or more triggering non-compliance metrics to perform one or more remediation actions; and inputting data including the one or more of a triggering non-compliance metrics, a process point in the BPM, and the roles being alerted, and data from the BPM into the triggered remediation prediction model. The remediation prediction model operates to implement remediation of non-compliance of the in-progress instance by one or more of: inserting a work item into a work list of one or more roles; sending a delay estimate to one or more roles; and receiving a delay estimate from a role and updating the remediation model on the basis of the received delay estimate.

One advantage resides in performing real-time monitoring of an instance of a medical process or workflow and automatically determining compliance of one or more activities of the medical process or workflow.

Another advantage resides in automatically detecting noncompliance of one or more activities of a medical process or workflow and automatically generating role-specific alerts when the activities of a medical process or workflow are not in compliance.

Another advantage resides in automatically detecting noncompliance of one or more activities of a medical process or workflow and triggering a remedial process for remediating the noncompliance.

Another advantage resides in detecting deviations from processes of a medical process or workflow and generating alerts for caregivers.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

Figure 1:
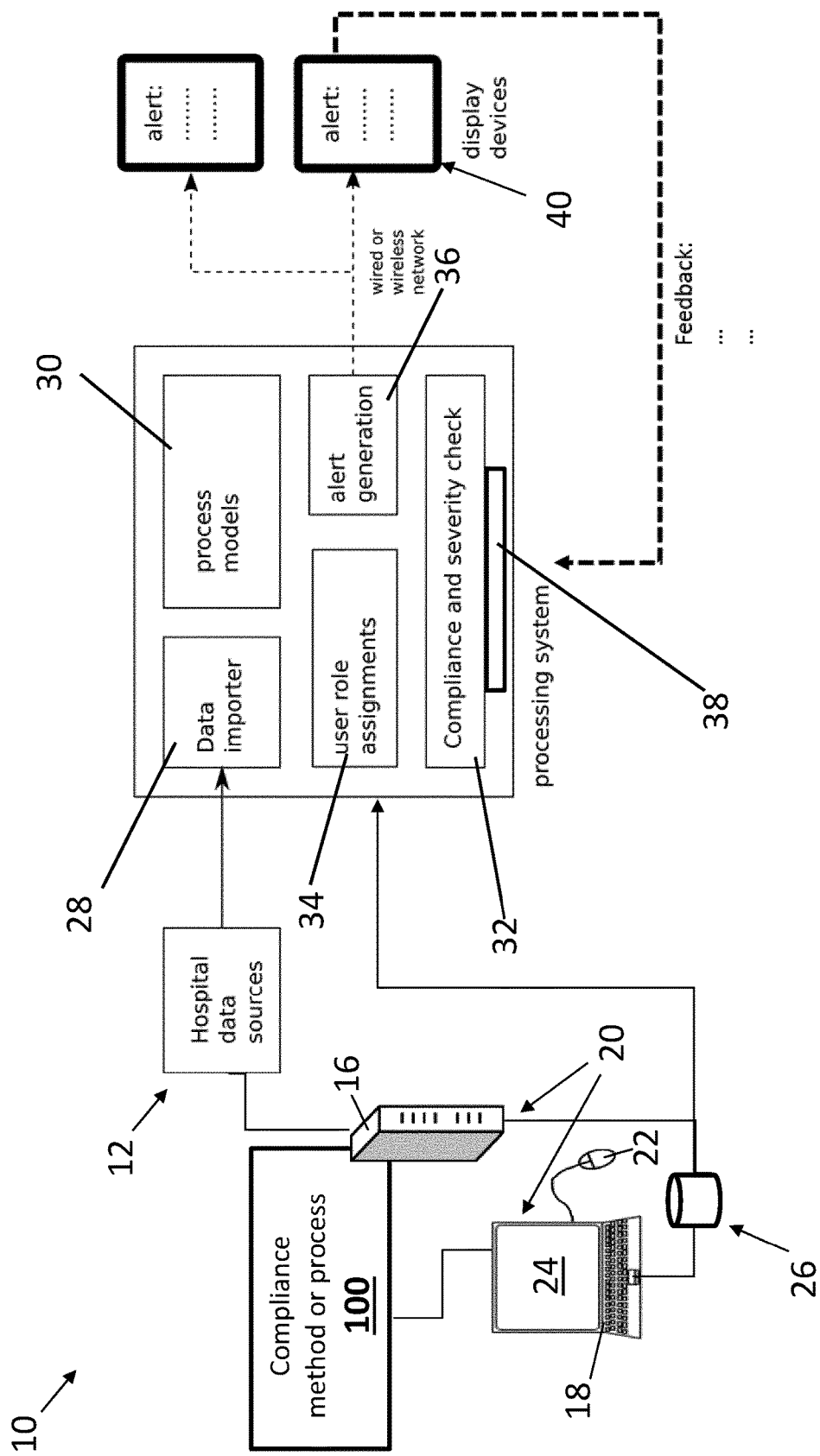
FIG. 1 diagrammatically shows a process compliance system according to one aspect.

Even when processes are defined for clinical operations (e.g., Business Process Models (BPMs), standard operating procedures (SOPs), etc.), it remains difficult to ensure the compliance to these definitions in everyday operations if the enactment of the processes is not implemented by a Workflow Management System. For example, it may be difficult for all the persons involved in a process to keep track of the execution of each step in each process and decide where it would be necessary to take remediation action. In embodiments disclosed herein, role-specific non-compliance alerts in the context of medical processes, such as the process or workflow of a patient undergoing a particular imaging procedure, are provided. This is done by leveraging a Business Process Model (BPM) of the process or workflow to track events in real-time, in conjunction with added components to detect non-compliance and auxiliary models to monitor remediation of non-compliance.

A BPM is a model of a process or workflow in which nodes or blocks represent activities, events, decision points (e.g. gateways), and so forth, and connections indicate flow of the process and/or data into or out of the process. BPMs receive input from data sources (e.g., mined from the various hospital databases in the case of a BPM representing a medical process or workflow) and provide real-time monitoring of the process as modeled by a model. A common BPM formalism is Business Process Model and Notation (BPMN) (e.g. BPMN 2.0, available from Object Management Group, Needham, MA, USA) which uses a block diagram notation constructed by user employing a graphical user interface. A BPMN representation of a process typically employs elements such as: flow objects representing events which occur or activities to be done; gateways representing the forking or merging of paths; connectors representing process flow, data flow, or linking flow objects; grouping elements such as swim lanes; and/or so forth. The BPM for a given medical process or workflow is typically generated by a user interacting with a graphical user interface (GUI) which enables the user to construct the BPM by adding and configuring elements and connectors. The BPM modeling GUI may be preconfigured for the given hospital or other medical facility, e.g. providing automatic connection of an element to the appropriate medical databases for receiving data to be processed at the element and for outputting data generated at the element to appropriate databases. The BPM is, in embodiments disclosed herein, preferably labeled as to roles and resources deployed in each process block.

As used herein, the term "medical process or workflow" or similar phraseology is used to indicate a medical process or workflow which is modeled by a BPM. An "instance" of the medical process or workflow refers to a particular instance in which the medical process or workflow is performed. For example, a radiology examination process or workflow for a particular type of radiology examination may be modeled by a BPM. When a specific patient undergoes the radiology examination this is referred to herein as an instance of the radiology examination. The BPM models a specific medical process or workflow, and is applied to monitor a given instance of the modeled medical process or workflow in real time. As used herein, "real time" is to be understood as allowing for practical delays, e.g. if the process or workflow calls for a blood draw event then detection of that event in the instance of the process or workflow may occur when the nurse enters the blood draw into an electronic medical record which may happen some time after the actual action of drawing the blood sample. It will be appreciated that multiple instances may be occurring concurrently, e.g. more than one patient may be undergoing the same radiology examination at the same time, and the monitoring of each such patient using the BPM is then an instance of the BPM.

To provide monitoring to detect non-compliance with the design-basis process, in embodiments disclosed herein the BPM is modified or augmented to define non-compliance metrics such as deviations from the expected, minimum, and/or maximum time delay between each pair of connected activities, deviations from the correct time sequence of activities, failure to perform a necessary activity, performance of an unnecessary activity, and/or so forth. The values for these non-compliance metrics are monitored in real time, and are suitably formulated as a non-compliance vector c of length n (where n is the number of non-compliance metrics).

In some embodiments disclosed herein, the non-compliance vector c is leveraged to identify the role or roles that need to be notified in the event of a non-compliance. To do so, an m×n matrix M is constructed, where m is the number of roles. The roles to alert are determined as an alert vector a suitably given by a=M c, where the alert vector a is of length m. Each horizontal row of the matrix M represents a role (there are m horizontal rows), and within each row each column element stores a weight indicating the importance (i.e. need of notification) of the role of that row for the compliance metric of that column (there are n vertical columns). The corresponding element of the per-role compliance vector s is then a sum over the n compliance metrics, weighted by the weights given in the matrix M, and indicates whether that role should receive an alert. In general, the matrix M may be a function of the process point in the BPM at which the alert vector a is determined. Rather than (or in addition to) multiplying Mc to generate the alert vector a, in another contemplated approach a particular element i of the non-compliance vector c is detected to be above threshold so as to indicate the corresponding type of noncompliance is at a level calling for remediation. Then, the m elements of the ith column of the matrix M is consulted to determine the significance weights of the type of noncompliance indexed by i for each of the m roles.

In some embodiments disclosed herein, an alert is generated if any element of the non-compliance vector c is over a specified threshold. The specific alert (or alerts) to be generated is determined by thresholding the elements of the non-compliance vector c to determine the type of non-compliance, and the recipients of the alert are determined from the element(s) of the alert vector a that are over threshold. The type of non-compliance may be converted to a specific alert message via a look-up table or the like. These alert messages may be pushed to the role (e.g., to staff of a clinical department, patient transport department, or so forth) as text messages, emails, or so forth.

The generation of an alert to one or more roles optionally also triggers execution of a remediation prediction model for the particular type of non-compliance. The remediation prediction model takes as inputs at least the triggering non-compliance metric, and may also take as inputs information such as the process point in the BPM, the role(s) being alerted (from the alerts vector a) and data extracted from the BPM. The remediation prediction model may be programmed to perform various tasks such as placing work items onto worklists of the various roles and sending alerts to downstream role players to inform them of an expected delay (estimated statistically by the prediction model, or received directly from an actor involved in the delay). The remediation prediction model may also receive feedback on the remediation process, for example if a text message is pushed to a lab indicating it needs to perform a certain test on a patient the lab may text back with an estimate of when the test will be completed which then is input to the remediation prediction model to update the predicted remediation timeframe.

With reference to FIG. 1, an illustrative process compliance and role-specific alerting system 10 is shown. As shown in FIG. 1, the system 10 includes one or more databases 12. The database(s) 12 can be any suitable database, such as a Health-Level 7 (HL7)-compliant database, a Picture Archiving and Communication System (PACS) storing radiology examination data including medical images in Digital Imaging and Communications in Medicine (DICOM) format, a Radiological Information System (RIS) database, an Electronic Medical Record (EMR) or similar database such as an Electronic Health Record (EHR), various clerical databases such as a hospital admissions and/or human resources databases, various combinations thereof, and so forth.

FIG. 1 also shows an electronic processor 20 operatively connected with the database 12. The electronic processor 20 can be any suitable processor, typically a server computer 16 or a plurality of server computers, e.g. interconnected to form a server cluster, cloud computing resource, or so forth), although the electronic processor 20 may be alternatively or additionally embodied as a computing device 18 (e.g., typically a workstation computer, or more generally a computer, although another form factor such as a tablet, a smartphone, and so forth is also contemplated). While a single server 16 is illustrated, it will be appreciated that the desired computing capacity may be obtained by way of a plurality of cooperating server computers, e.g. a computing cluster, cloud computing resource, or so forth, and it is to be understood that the server computer 16 encompasses such multi-computer embodiments.

The illustrative workstation 18 comprises a computer or other electronic data processing device with typical components, such as at least one microprocessor, at least one user input device (e.g., a mouse, a keyboard, a trackball, and/or the like) 22, and a display device 24 (e.g. an LCD display, plasma display, cathode ray tube display, and/or so forth). It should be noted that these components can be variously distributed. For example, the electronic processor 20 may include a local processor of a workstation terminal and the processor of a server computer that is accessed by the workstation terminal. In some embodiments, the display device 24 can be a separate component from the workstation 18. The database 12 stores data related to a medical process or workflow, which can be graphically displayed on a BPM (e.g., on the display device 24). The BPM is generated semi-manually, using a graphical user interface (GUI) to connect nodes as a flowchart.

The electronic processor 20 is operatively connected with one or more non-transitory storage media 26. The non-transitory storage media 26 may, by way of non-limiting illustrative example, include one or more of a magnetic disk, RAID, or other magnetic storage medium; a solid state drive, flash drive, electronically erasable read-only memory (EEROM) or other electronic memory; an optical disk or other optical storage; various combinations thereof; or so forth; and may be for example a network storage accessible by the server 16, an internal hard drive of the workstation 18, various combinations thereof, or so forth. It is to be understood that any reference to a non-transitory medium or media 26 herein is to be broadly construed as encompassing a single medium or multiple media of the same or different types. Likewise, the electronic processor 20 may be embodied as a single electronic processor or as two or more electronic processors (e.g. the server 16 and processor of the workstation 18).

The system 10 is configured to perform a medical process or workflow compliance monitoring method or process 100. The non-transitory storage medium 26 stores instructions which are readable and executable by the at least one electronic processor 20 and to perform disclosed operations including performing the medical process or workflow compliance monitoring method or process 100. In some examples, the method 100 may be performed at least in part by cloud processing.

The instructions which are executed to perform the medical process or workflow compliance monitoring method or process 100 may be viewed as implementing (i) a data importer 28; (ii) a process storage 30; (iii) a compliance evaluation module 32; a user role assignment module 34; an alert generation module 36; and a remediation model storage 38.

The process storage 30 is configured to store one or more process models (e.g., template models) representing processes to be followed during medical process or workflow operations. In a practical implementation, there can be many process models for monitoring a corresponding number of many different medical processes or workflows; a single illustrative process model is discussed here for simplicity, and is assumed to be implemented as a BPM which employs BPMN notation in illustrative examples herein. Such process models can include complex elements like branching, decisions, loops, parallel paths. In addition to the connection of the activities, the expected, minimum, and maximum time delay between each pair of connected activities can also be part of the model.

The BPM is configured to receive data imported by the data importer 28 from the database(s) 12. The data is imported such that respective records of the data can be assigned to activities in the process models stored in the process storage 30. Usually such assignments are defined by the configuration of the various elements of the BPM which identify data sources consumed by the various event elements, activity elements, gateway elements, or other elements of the BPM. As a non-limiting illustrative example, an event element representing transfer of the patient from a bedside medical device (e.g. bedside intravenous pump) to a portable medical device consume the log entry of this transfer in the patient's EMR, and this event may start a timer which measures the time until an arrival event which detects arrival of the patient at the radiology lab, for example by reading the patient sign-in log of the radiology lab. As another example, a blood test event may detect when a laboratory test result is entered in the patient's EMR, and has a binary output of "1" indicating the test result is available or "0" indicating it is not available. These are merely two non-limiting illustrative examples.

A compliance evaluation module 32 checks the compliance of the imported medical process or workflow data (in some cases processed with the activities in the process models, e.g. as in the example of measuring a time between two events given above). Data imported directly from the hospital data source(s) 12 and/or processed by the BPM is checked to ensure compliance with sequences of medical process or workflow activities, omitted medical process or workflow activities, additional medical process or workflow activities, repeated medical process or workflow activities, unnecessary medical process or workflow activities (i.e., belonging to a different branch of the model), and/or time delay between pairs of medical process or workflow activities, as defined and monitored by the BPM. In one example, the (non-)compliance with the template model can be expressed by a non-compliance vector c of length n number of parameters used to measure compliance.

The user role assignment module 34 is configured to evaluate the non-compliance vector c to determine role-specific notification (i.e. alert) outputs. The alerts are determined based on a per-role basis (i.e., for each staff role, the severity (or need for action) is determined separately). In an illustrative approach, with m representing a number of considered staff roles, a matrix M of dimensions m×n is employed, and a role assignments vector a is determined as the matrix M multiplied by the non-compliance vector c for the m roles (that is, a=Mc where a is an alert vector of length m) as shown below:

$$\begin{bmatrix} a_1 \\ a_2 \\ \vdots \\ a_m \end{bmatrix} = \begin{bmatrix} m_{1,1} & \cdots & m_{1,n} \\ \vdots & \ddots & \vdots \\ m_{m,1} & \cdots & m_{m,n} \end{bmatrix} \begin{bmatrix} c_1 \\ c_2 \\ \vdots \\ c_n \end{bmatrix}$$

The ith element of the non-compliance vector c (that is, vector element $c_i$) indicates the severity of the noncompliance of type i. As can be seen in the above expression, the ith column of matrix M has elements ($m_{1,i}, m_{2,i}, \ldots, m_{m,i}$), may then be viewed as storing the relative importance of the noncompliance of type i amongst the m roles. The product Mc gives the alerts vector a, whose elements indicate the need for alerting each role 1, ..., m. A high value from the role assignments vector a corresponds to a greater need for action to remediate the noncompliance (or at least a greater need for awareness of the noncompliance) by the respective role. As used herein, the roles m can include, for example, (1) an individual person playing a role; (2) a medical department playing a role; (3) some other grouping of medical personnel (e.g. all imaging technicians currently active in a radiology laboratory); or so forth; among others.

The alert generation module 36 is configured to generate an alert based on the determined severity of the non-compliance (e.g., represented by elements of the non-compliance vector c) when the severity vector s exceeds a predetermined threshold. Each role m has an individual predetermined threshold. When the threshold(s) is exceeded, an alert is sent to one or more staff members (or, more generally, roles). The alert can be indicative of an identification of the non-compliant activity of the medical process or workflow, a severity score, an explanation explaining what factors triggered the alert, a description of a remediation action, an indication of which staff members received the alert, and so forth. The alert can be, for example, a Messaging Service (MS) text message, a Short Messaging Service (SMS), automated telephone call, an alert in a web-based program such as Microsoft Outlook, and so forth in order to inform a staff member of non-compliance of the medical process or workflow. The alerts can be output to an output alert device 40 (e.g., the display device 24, a smartphone, a tablet, and so forth).

If the role is some group of persons, then alert may go to personal electronic devices of all members of the group (e.g. an alert to a role consisting of the nurses of a patient ward may be sent as an SMS message sent to the cellphones of all nurses on duty in the patient ward) and/or may go to some central device (e.g. the alert may additionally or alternatively be sent to a central nurses' station of the patient's ward). It should be noted that the alerts are sent on a per-role basis, and may be different for different roles. Hence, for example, if in a process or workflow a patient is detected as being readied for transport to the radiology lab but it is detected that a vital sign reading required in the process or workflow has not yet been acquired, then this may trigger an alert to the nursing staff at the patient's ward to acquire the vital sign reading and an alert to clerical staff of the radiology lab notifying the radiology lab that the patient's arrival is estimated to be delayed by 15 minutes (where this delay time is estimated based on the amount of time it typically, i.e. statistically, takes to acquire the vital sign reading).

The optional remediation model storage 38 stores remediation prediction models for corresponding non-compliance metrics which triggered an alert. The remediation prediction models describe actions to address the non-compliance metrics. The remediation prediction models can include actions to address compliance issues, such as (by way of non-limiting illustrative example) inserting a work item into a work list of one or more roles; updating an existing work item of one or more roles; adjusting a schedule of one or more roles (e.g., if a patient arrival is delayed, that patient may be rescheduled for a later time slot and, if possible, a patient from a later time slot may be rescheduled into the now-open time slot vacated by the delayed patient); sending a delay estimate to one or more roles; receiving a delay estimate from a role and updating the remediation model on the basis of the received delay estimate, among others.

Figure 2:
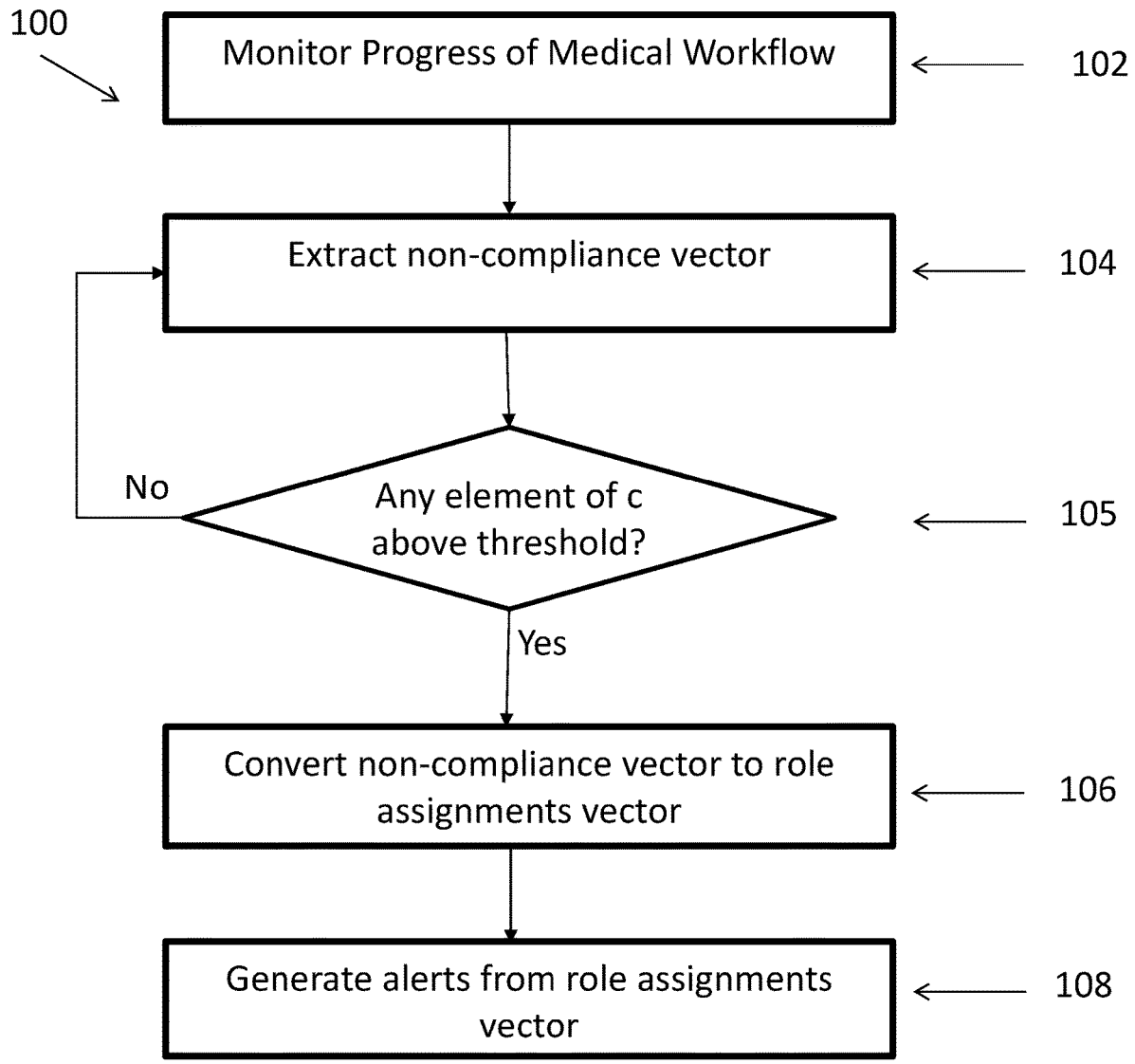
FIG. 2 shows exemplary flow chart operations of the system of FIG. 1.

With reference to FIG. 2, an illustrative embodiment of an instance of the medical process or workflow compliance monitoring method 100 executable by the at least one electronic processor 20 is diagrammatically shown as a flowchart. At 102, progress of an in-progress instance of a medical process or workflow is monitored using a BPM (e.g., stored in the process storage 30) that includes a number of defined roles m in the medical process or workflow is monitored (e.g., by importing data from the database 12 using the data importer 28). For example, the medical process or workflow may be a brain imaging process or workflow. An instance of such a process or workflow would then be a specific patient undergoing that brain imaging process or workflow.

At 104, a non-compliance vector c is extracted from the BPM during the monitoring of the in-progress instance (e.g., executed by the compliance evaluation module 32). The non-compliance vector c includes vector elements storing values of non-compliance metrics for the in-progress instance. The non-compliance metrics can include one or more of a value indicative of an omission of an activity required in the BPM; a time delay between a pair of connected activities of the BPM that is below a minimum time delay between the connected activities defined in the BPM; a time delay between a pair of connected activities of the BPM that is above a maximum time delay between the connected activities defined in the BPM; a value indicative of a deviation from a time sequence of activities defined in the BPM; and a value indicative of performance of an activity not required in the BPM, among others. At decision 105, each element of the non-compliance vector c is thresholded to detect whether any type of noncompliance is at a sufficient severity to require remediation. As long as no non-compliance requiring remediation is detected at 105, flow returns to 104 to continuously update the non-compliance vector c.

On the other hand, if at 105 any element of the non-compliance vector c is found to indicate remediation is required, then at 106, the non-compliance vector c is converted to a role assignments vector a whose vector elements store values indicative of role assignments for remediating non-compliance of the in-progress instance (e.g., executed by the user role assignment module 34). For example, the non-compliance vector c has n elements corresponding to n non-compliance metrics. The role assignments vector a has m elements corresponding to m roles. The converting of the non-compliance vector c to the role assignments vector a includes multiplying the non-compliance vector by an m×n transformation matrix M. The matrix M includes m rows representing the number of m defined roles in the BPM and n columns representing the number of n non-compliance metrics. Each row of the m×n matrix M stores a corresponding weight associated with the corresponding role m. The weight indicates a need of notification of the role m for the remediating the non-compliance metric in the respective column of the matrix M.

At 108, one or more alerts directed to one or more roles m on the basis of vector elements of the role assignments vector a (e.g., executed by the alert generation module 36). To do so, a type of non-compliance is determined from the non-compliance vector c, and one or more alerts are generated (for example, as text) corresponding to the type of non-compliance.

In one example, the plurality of non-compliance metrics are each compared to a corresponding predefined alert threshold to determine whether the metrics are non-compliant. An alert is generated when at least one of the plurality of non-compliance metrics is above the corresponding predefined alert threshold. The alert can be generated as one of a text message, alert, or notification to one or more staff members of a clinical department or a patient transport department. In some embodiments, a look-up table (e.g., stored in the non-transitory computer readable medium 26) is used to determine whether the at least one of the plurality of non-compliance metrics is above the corresponding predefined alert threshold.

In another example, a remediation prediction model for corresponding one or more triggering non-compliance metrics (e.g., stored in the remediation model storage 38) is triggered to perform one or more remediation actions. Data, including the one or more of a triggering non-compliance metrics, a process point in the BPM, and the roles being alerted, and data from the BPM, are input into the triggered remediation prediction model. The remediation prediction model operates to implement remediation of non-compliance of the in-progress instance by one or more of: inserting a work item into a work list of one or more roles; sending a delay estimate to one or more roles; and receiving a delay estimate from a role and updating the remediation model on the basis of the received delay estimate.

In some embodiments, the system 10 can also calculate a prediction for further process execution and expected time delays. This can be performed by using machine learning on historical data of process execution. This additional information about the predicted further execution is then also connected with alert decisions.

In some embodiments, the roles m are assigned to individuals. For example, not all technicians can receive an alert about a delay in an imaging procedure, but only an individual technician responsible for the respective patient.

In some embodiments, feedback is gathered from one or more individuals who have received an alert (see FIG. 1). Feedback can be provided to the system 10 in form of short message services or other pre-defined data connections between processing system and the output display devices 40. Feedback messages may include one or more of the following: medical process or workflow information received; ability to perform a remediation action, a time to perform a remediation action; determine who should perform a remediation action, and how the remediation action should be formed. Feedback messages are important for the advanced prediction of process alterations, further executions, and delays.

In one example, a computed tomography (CT) medical process or workflow process requires that a lab examination is performed before the CT imaging procedure. A patient transport service is requested to retrieve a patient to be imaged for transport to the radiology department. The system 10 identifies a non-compliance (using the processes described above), as the patient had not undergone a lab examination. Based on the role-based severity evaluation, one alert is sent to transport service, so that the transport is stopped. A second alert is sent to the nurse to get a blood sample. A third alert is sent to the radiology staff to inform about the expected delay.

The disclosure has been described with reference to the preferred embodiments. Modifications and alterations may occur to others upon reading and understanding the preceding detailed description. It is intended that the disclosure be construed as including all such modifications and alterations insofar as they come within the scope of the appended claims or the equivalents thereof.

The invention claimed is:

1. A non-transitory computer readable medium storing instructions executable by at least one electronic processor to perform a medical process or workflow compliance monitoring and remediation method, the method comprising:
   executing a Business Process Model (BPM) in real-time during a medical process or workflow carried out by a medical staff, wherein the BPM models a number of defined role assignments of the medical staff in the medical process or workflow, and wherein executing the BPM includes mining data stored during the medical process or workflow over a server network in at least one database, and monitoring in real-time from the mined data a progress of an in-progress instance of the medical process or workflow;
   extracting a non-compliance vector (c) from the BPM during the monitoring of the in-progress instance, the non-compliance vector comprising vector elements storing values of non-compliance metrics for the in-progress instance;
   converting the non-compliance vector to a role assignments vector (a) whose vector elements store values indicative of remedial role assignments for remediating non-compliance of the in-progress instance; and
   generating one or more alerts over the server network to the medical staff, the one or more alerts describing one or more roles of the remedial role assignments on the basis of the vector elements of the role assignments vector.

2. The non-transitory computer readable medium of claim 1, wherein the generating of the one or more alerts includes:
   determining a type of non-compliance from the non-compliance vector (c); and
   generating the one or more alerts as text corresponding to the type of non-compliance.

3. The non-transitory computer readable medium of claim 1, wherein the non-compliance metrics include one or more of:
   a value indicative of an omission of an activity required in the BPM;
   a time delay between a pair of connected activities of the BPM that is below a minimum time delay between the connected activities defined in the BPM;
   a time delay between a pair of connected activities of the BPM that is above a maximum time delay between the connected activities defined in the BPM;
   a value indicative of a deviation from a time sequence of activities defined in the BPM; and
   a value indicative of performance of an activity not required in the BPM.

4. The non-transitory computer readable medium of claim 2, wherein the non-compliance vector (c) has n elements corresponding to n non-compliance metrics, the role assignments vector (a) has m elements corresponding to m roles, and the converting of the non-compliance vector to the role assignments vector includes:
   multiplying the non-compliance vector by an m×n transformation matrix (M).

5. The non-transitory computer readable medium of claim 4, wherein:
   the matrix (M) includes m rows representing the number of m defined roles in the BPM and n columns representing the number of n non-compliance metrics; and
   each row of the m×n matrix (M) stores corresponding weights associated with the corresponding role, each weight indicating a need of notification of the role for the remediating the non-compliance metric in the respective column of the matrix.

6. The non-transitory computer readable medium of claim 4, wherein the generating of the alerts further includes:
   determining whether at least one of the plurality of non-compliance metrics is above a corresponding predefined alert threshold; and
   generating an alert when the at least one of the plurality of non-compliance metrics is above a predefined alert threshold, the alert including one of a text message, alert, or notification to one or more staff members of a clinical department or a patient transport department.

7. The non-transitory computer readable medium of claim 6, wherein the determining includes:
   using a lookup table to determine whether the at least one of the plurality of non-compliance metrics is above the corresponding predefined alert threshold.

8. The non-transitory computer readable medium of claim 1, wherein the generating of the one or more alerts includes:
   triggering a remediation prediction model for corresponding one or more triggering non-compliance metrics to perform one or more remediation actions; and
   inputting data including the one or more of a triggering non-compliance metrics, a process point in the BPM, and the roles being alerted, and data from the BPM into the triggered remediation prediction model.

9. The non-transitory computer readable medium of claim 8, wherein the remediation prediction model operates to implement remediation of non-compliance of the in-progress instance by one or more of:

inserting a work item into a work list of one or more roles;
sending a delay estimate to one or more roles; and
receiving a delay estimate from a role and updating the remediation model on the basis of the received delay estimate.

10. A process compliance system for determining compliance and remediating non-compliance with a medical process or workflow, the system comprising:
at least one electronic processor connected to a server network;
a non-transitory computer readable medium storing instructions executable by the least one electronic processor to perform a medical process or workflow compliance monitoring method, the instructions comprising:
instructions for executing a Business Process Model (BPM) in real-time during a medical process or workflow carried out by a medical staff, wherein the BPM models a number of defined role assignments of the medical staff in the medical process or workflow, and wherein executing the BPM includes mining data stored during the medical process or workflow over a server network in at least one database, and monitoring in real-time from the mined data a progress of an in-progress instance of the medical process or workflow;
instructions for extracting a non-compliance vector (c) from the BPM during the monitoring of the in-progress instance, the non-compliance vector comprising vector elements storing values of non-compliance metrics for the in-progress instance, the non-compliance vector having n elements corresponding to n non-compliance metrics;
instructions for converting the non-compliance vector to a role assignments vector (a) whose vector elements store values indicative of remedial role assignments for remediating non-compliance of the in-progress instance, the role assignments vector having m elements corresponding to m roles, the converting including multiplying the non-compliance vector by an m×n transformation matrix (M); and
instructions for generating one or more alerts over the server network to the medical staff, the one or more alerts describing one or more roles of the remedial role assignments on the basis of the vector elements of the role assignments vector (a) based on a determination of a type of non-compliance from the non-compliance vector.

11. The system of claim 10, wherein the non-compliance metrics include one or more of:
a value indicative of an omission of an activity required in the BPM;
a time delay between a pair of connected activities of the BPM that is below a minimum time delay between the connected activities defined in the BPM;
a time delay between a pair of connected activities of the BPM that is above a maximum time delay between the connected activities defined in the BPM;
a value indicative of a deviation from a time sequence of activities defined in the BPM; and
a value indicative of performance of an activity not required in the BPM.

12. The system of claim 10, wherein:
the matrix (M) includes m rows representing the number of m defined roles in the BPM and n columns representing the number of n non-compliance metrics; and
each row of the m×n matrix (M) stores corresponding weights associated with the corresponding role, the weights indicating a corresponding need of notification of the role for the remediating the non-compliance metric in the respective column of the matrix.

13. The system of claim 10, wherein the instructions for generating the alerts further includes:
instructions for determining whether at least one of the plurality of non-compliance metrics is above a corresponding predefined alert threshold; and
instructions for generating an alert when the at least one of the plurality of non-compliance metrics is above a predefined alert threshold, the alert including one of a text message, alert, or notification to one or more staff members of a clinical department or a patient transport department.

14. The system of claim 13, wherein the instructions for determining includes:
using a lookup table to determine whether the at least one of the plurality of non-compliance metrics is above the corresponding predefined alert threshold.

15. The system of claim 10, wherein the instructions for generating of the one or more alerts includes:
instructions for triggering a remediation prediction model for corresponding one or more triggering non-compliance metrics to perform one or more remediation actions; and
instructions for inputting data including the one or more of a triggering non-compliance metrics, a process point in the BPM, and the roles being alerted, and data from the BPM into the triggered remediation prediction model.

16. The system of claim 15, wherein the remediation prediction model operates to implement remediation of non-compliance of the in-progress instance by one or more of:
inserting a work item into a work list of one or more roles;
sending a delay estimate to one or more roles; and
receiving a delay estimate from a role and updating the remediation model on the basis of the received delay estimate.

17. A medical process or workflow compliance monitoring method, comprising:
executing, by a processor connected to a server network, a Business Process Model (BPM) in real-time during a medical process or workflow carried out by a medical staff, wherein the BPM models a number of defined role assignments of the medical staff in the medical process or workflow, and wherein executing the BPM includes mining data stored during the medical process or workflow over a server network in at least one database, and monitoring a progress of an in-progress instance of the medical process or workflow;
extracting, by the processor, a non-compliance vector (c) from the BPM during the monitoring of the in-progress instance, the non-compliance vector comprising vector elements storing values of non-compliance metrics for the in-progress instance;
converting, by the processor, the non-compliance vector to a role assignments vector (a) whose vector elements store values indicative of remediation role assignments for remediating non-compliance of the in-progress instance; and
generating, by the processor, one or more alerts directed to one or more roles of the remediation role assignments on the basis of the vector elements of the role assignments vector, the generating including triggering a remediation prediction model for corresponding one or more triggering non-compliance metrics to perform one or more remediation actions; and inputting data including the one or more of a triggering non-compliance metrics, a process point in the BPM, and the roles being alerted, and data from the BPM into the triggered remediation prediction model;

wherein the remediation prediction model operates to implement remediation of non-compliance of the in-progress instance by one or more of: inserting a work item into a work list of one or more roles; sending a delay estimate to one or more roles; and receiving a delay estimate from a role and updating the remediation model on the basis of the received delay estimate.

18. The method of claim 17, wherein the non-compliance vector (c) has n elements corresponding to n non-compliance metrics, the role assignments vector (a) has m elements corresponding to m roles, and the converting of the non-compliance vector to the role assignments vector includes:

multiplying the non-compliance vector by an m×n transformation matrix (M).

19. The method of claim 18, wherein:

the matrix (M) includes m rows representing the number of m defined roles in the BPM and n columns representing the number of n non-compliance metrics; and each row of the m×n matrix (M) stores a corresponding weight associated with the corresponding role, the weight indicating a need of notification of the role for the remediating the non-compliance metric in the respective column of the matrix.

20. The method of claim 17, wherein the generating of the alerts further includes:

determining whether at least one of the plurality of non-compliance metrics is above a corresponding predefined alert threshold; and generating an alert when the at least one of the plurality of non-compliance metrics is above a predefined alert threshold, the alert including one of a text message, alert, or notification to one or more staff members of a clinical department or a patient transport department.

* * * * *